United States Patent [19]
Keresztes et al.

[11] Patent Number: 5,441,940
[45] Date of Patent: Aug. 15, 1995

[54] PROCESS FOR THE PREPARATION OF WATER SOLUBLE PRIMYCIN AND ITS COMPONENTS AND PHARMACEUTICAL COMPOSITIONS CONTAINING THEM

[75] Inventors: Tamás Keresztes, Frzsébet; András Kövér, Erzsébet; Gábor Kulcsár, Szlovák; Katalin Erdödiné, Nagyerdei; Gergelyné P. Katalin, Közép, all of Hungary

[73] Assignee: Chinoin Gyogyszer es Vegyeszeti Termekek Gyara Rt., Budapest, Hungary

[21] Appl. No.: 133,795

[22] Filed: Oct. 8, 1993

Related U.S. Application Data

[63] Continuation of Ser. No. 576,381, filed as PCT/HU89/00052, Nov. 17, 1989, abandoned.

[30] Foreign Application Priority Data

Nov. 18, 1988 [HU] Hungary ................ 5948/88

[51] Int. Cl.$^6$ ............ A61K 31/70; C07H 15/04
[52] U.S. Cl. ..................... 514/31; 536/6.5; 536/16.9
[58] Field of Search ............ 536/6.5, 16.9; 514/31

[56] References Cited

U.S. PATENT DOCUMENTS

| | | | |
|---|---|---|---|
| 2,793,978 | 5/1957 | Wachtel et al. | 536/16.9 |
| 4,677,097 | 6/1987 | Omura et al. | 536/7.2 |
| 4,782,141 | 11/1988 | Dekany et al. | 536/6.5 |
| 4,873,348 | 10/1989 | Szilágyi et al. | 549/271 |

Primary Examiner—Douglas W. Robinson
Assistant Examiner—Elli Peselev
Attorney, Agent, or Firm—Keil & Weinkauf

[57] ABSTRACT

The invention relates to a process for the preparation of water soluble primycin and to the separation of its components of formulae ($A_1$) and ($A_3$) either as single components or as a mixture of the two components. According to the invention (i) water insoluble primycin is reacted in a $C_{1-3}$ alcohol with a condensable substance comprising a C—C—C bridge in the presence of sodium or potassium methoxide or ethoxide, the resulting product with a water solubility of 40–60 mg/ml is separated, and, if desired, (ii) the resulting substance is subjected to column chromatography on silica gel applying a 1% aqueous solution of Partridge mixture as eluting agent to obtain a mixture of components of formulae ($A_1$) and ($A_3$) with a water solubility of 50 mg/ml, and, if desired, (iii) the resulting two-component mixture is subjected to ion exchange chromatography applying carboxymethyl cellulose in ammonium cycle as adsorbent and eluting the adsorbent with aqueous ammonium hydrocarbonate solution to obtain the component of formula ($A_3$) with a water solubility of 50 mg/ml in pure form, and, if desired, (iv) elution is continued with absolute methanol comprising 10 mmoles of acetic acid to obtain the component of formula ($A_1$) with a water solubility of 10 mg/ml in pure form.

15 Claims, 13 Drawing Sheets

PROCESS FOR THE PREPARATION OF WATER SOLUBLE PRIMYCIN AND ITS COMPONENTS AND PHARMACEUTICAL COMPOSITIONS CONTAINING THEM

This application is a continuation of application Ser. No. 07/576,381, filed as PCT/HU89/00052, Nov. 17, 1989 now abandoned.

The invention relates to a process for the preparation of water soluble primycin and to the separation of its individual components. The invention also relates to pharmaceutical and veterinary compositions comprising water soluble primycin or its components as active ingredient(s).

Primycin is a widely applied antibiotic with strong antimicrobial activity. Its empirical formula has been disclosed by J. Aberhart et al. [J. Am. Chem. Soc. 92, 5816 (1970)]; the authors have also given the supposed structural formula of primycin. Subsequent investigations have revealed, however, that primicyn antibiotic is a mixture comprising three major components and at least ten minor components [J. Chromatogr. 295, 141-151 (1984)]. The term "primycin", whenever used in the specification and claims, refers to this multicomponent mixture; the individual components of the mixture are marked by specific code letters.

Many papers deal with the preparation of primycin and its components, of which, over the references cited above, Hungarian patents Nos. 146,332, 153,593, 158,241, 177,299, 194,493 and 195,514 are mentioned. Primycin and its components prepared according to all of the methods known so far are sparingly soluble in water, which involves several difficulties when applying them in the therapy, since it enables one to prepare pharmaceutical compositions with rather low active agent contents (thus e.g. the active agent content of the well known primycin-containing Embrimycin$^R$ Gel is only 0.2%). As a further disadvantage, the separation of the individual components of primycin requires lengthy and sophisticated operations.

Our aim was to convert primycin, prepared e.g. as described in Hungarian patents Nos. 146,332 and 153,593, into a water soluble substance by a simple and economic method. Our aim was further to separate two of the major components of primycin either individually or as a mixture by a simple operation.

According to the invention one proceeds as follows:
(i) water insoluble primycin is reacted in a $C_{1-3}$ alcohol, preferably in ethanol, with a condensable substance comprising a C—C—C bridge, preferably with ethyl cyanoacetate, in the presence of sodium or potassium methoxide or ethoxide, preferably of sodium methoxide, the resulting product with a water solubility of 40–60 mg/ml is separated, and, if desired,
(ii) the resulting substance is subjected to column chromatography on silica gel applying an about 1% aqueous solution of Partridge mixture as eluting agent to obtain a mixture of components of formulae ($A_1$) and ($A_3$) with a water solubility of about 50 mg/ml, and, if desired,
(iii) the resulting two-component mixture is subjected to ion exchange chromatography applying carboxymethyl cellulose in ammonium cycle as adsorbent and eluting the adsorbent with aqueous ammoniumhydrocarbonate solution to obtain the component of formula ($A_3$) with a water solubility of about 50 mg/ml in pure form, and, if desired,
(iv) elution is continued with absolute methanol comprising/about 10 mmoles of acetic acid to obtain the component of formula ($A_1$) with a water solubility of/about 10 mg/ml in pure form.

Both the empirical formula and the thin layer chromatogram of water soluble primycin, obtained in the first step of the method of the invention, are identical with that of the starting substance, the only difference is the radical change in water solubility. The reasons for this fact are not fully elucidated, it is believed, however, that the sterical positions of the —OH groups of the starting primycin change upon the treatment according to the invention, which results in the abrupt increase of water solubility. The two major components of primycin, i.e. compounds of formulae ($A_1$) and ($A_3$), separated from the resulting water soluble primycin are also water soluble, and their empirical formulae are the same as disclosed in the literature.

Water soluble primycin and its components prepared according to the invention can be applied to advantage for therapeutical purposes, since they retain the excellent antimicrobial effects of the corresponding water insoluble substances, and enable one to prepare pharmaceutical compositions with much higher active agent content than before, e.g. aqueous solutions comprising even 50–100 mg/ml of active agent.

The invention also relates to pharmaceutical or veterinary compositions comprising as active agent water soluble primycin or a water soluble mixture of the components of formulae ($A_1$) and ($A_3$) or a water soluble single compound of formula ($A_1$) or ($A_3$) together with a pharmaceutically acceptable carrier, diluent or other auxiliary agent.

A more detailed description of the method of the invention is given below.

Water insoluble primycin prepared according to Hungarian patents Nos. 146,332 and 153,593 is applied as starting substance in the method of the invention. This substance has ionophoric properties.

Our previous investigations have revealed that, as a function of concentration and time, water insoluble primycin introduced in a concentration of 1–10-/umoles/ml blocks the repose $K^+$ channels of the surface membrane of skeletal muscles. This results in a decrease of membrane potential, which involves the functional change of contractile system, too. Primycin antibiotic has the unique structural characteristic that the molecule with high complexity comprises a guanidine moiety and an arabinose moiety; thus both the biological effects and the physico-chemical characteristics of the molecule are determined by the non-polyene type macrolide lactone and by the guanidine and arabinose moieties attached thereto. These parts of the molecule define jointly, through their amphipatic (i.e. hydrophilic and hydrophobic) properties, the orientation and binding of the antibiotic to the membrane. It can also be assumed that the channel-forming property of primycin is connected with the formation of dimers or higher polymers.

A partial or complete upsetting of the above interactions may considerably influence the polarity of the molecule and thus its solubility conditions, too, The partial or complete protonation of the guanidine moiety of the molecule may considerably influence the surface charge distribution (gross polarity), which, either directly or indirectly, may suppress or even enhance the appearance of intermolecular interactions.

To elaborate the first step of the method according to the invention we have performed about 150 experiments utilizing condensation reactions widely applied in the synthesis of compounds with pyrimidine skeleton. A common characteristic of these reactions is that the heteroaromatic ring is formed from a compound comprising an N—C—N or C—C—C bridge.

As compounds with C—C—C bridge e.g. propargyl aldehyde, ethyl formylacetate, ethyl cyanoacetate, malonic acid dinitrile, methyl ethynyl ketone, acetyl acetone and formyl-β-ethoxy propionic acid esters can be applied, of which ethyl cyanoacetate proved to be particularly preferable. As reaction medium dry (anhydrous) alcohols of 1 to 3 carbon atoms can be applied. The reaction is performed preferably in absolute ethanol, which can be prepared from predried ethanol by Grignard reaction. As a general rule, the dry solvents utilized in our experiments have been stored over a molecular sieve (such as Sigma molecular sieve with a pore diameter of 3–4 Å).

As catalyst, sodium or potassium methoxide or ethoxide, preferably sodium methoxide, can be applied.

When utilizing ethanol as reaction medium and maintaining the mixture under reflux, the reaction requires about 3–6 hours. At the end of this reaction time the reaction mixture is decolourized with activated carbon (Charcoal activ., Merck), filtered (preferably through a GF/C Whatman glass microfibre paper), and partially evaporated in vacuo. Evaporation can be performed e.g. in a Rotavapor R 110 (Büchi) apparatus.

Ethanol applied as reaction medium is continuously changed for dry methanol during the evaporation procedure, and then absolute ether and acetone are added to the concentrate to precipitate the product. A white solid is obtained, which is pulverized and stored for 24 hours in a vacuum drying pistol ("Blaugel", chloroform/ethanol, 65° C.) to obtain a sample for identification and analysis.

The characteristic data of the resulting water soluble primycin, compared to the water insoluble starting substance, are summarized in Table I below.

TABLE I

| | Water insoluble starting primycin | Water soluble primycin product |
|---|---|---|
| Empirical formula | $C_{55}H_{104}N_3O_{17}$ | $C_{55}H_{104}N_3O_{17}$ |
| Melting point | 180–184° C. | 162–164° C. |
| Biological activity measured as minimum inhibitory concentration (MIC) against *Bacillus subtilis* | 0.05 μg/ml | 0.1–0.5 μg/ml |
| Water solubility | 0.04 mg/ml | 40–60 mg/ml |

It appears from the empirical formula of the resulting water soluble primycin that the condensation reaction performed under the conditions of the synthesis of pyrimidine compounds does not result in ring closure, i.e. the supposed heteroaromatic ring does not form. It is likely that the reaction proceeds through the formation of an "intermediate" which basically changes the orientation of the —OH groups of the macrolide ring. It is assumed that this change results in the considerable increase of water solubility, and also this change enables one to separate the major components by a relatively simple operation. A possible explanation for this phenomenon is presented later.

The method of the invention enables one to prepare water soluble primycin in a reproducible manner from water insoluble primycin of any origin, without any previous purification of the starting substance. It is particularly preferred to apply water insoluble primycin contaminated with lead as starting substance. Namely it has been observed that the presence of lead favourably influences both the yield of water soluble primycin (which is generally 80–85%) and the maximum attainable water solubility (which is 50–100 mg/ml).

Based on atomic absorption spectroscopy (Perkin-Elmer Mod.) non-purified starting primycin comprises about 6–10 ppm of lead contamination. If a purified water insoluble primycin of therapeutical grade (such as Ebrimycin[R]) is utilized as starting substance, the yield of water soluble primycin decreases to about 50–60%, and a maximum water solubility of only 5–10 mg/ml can be attained. Therefore, if a purified water insoluble primycin is applied as starting substance, it is preferred to add 15–20 ppm of lead to the reaction mixture in the form of a soluble lead compound, preferably lead acetate.

Water soluble primycin has a further very interesting characteristic. It has been observed that its aqueous solution spontaneously gellifies, the gelling time being dependent on the primycin content of the solution. The extent of gelling, as a function of time and primycin concentration, is shown in FIG. 1. As it appears from the curves of FIG. 1, the complete gelling of a 5–10 mg/ml aqueous primycin solution requires about 1–2 days, that of a 20–40 mg/ml primycin solution requires about 6–12 hours, whereas an aqueous primycin solution comprising more than 50 mg/ml of primycin completely gellifies even within 1–2 hours. The effect of temperature on gelling is shown in FIG. 2. The concentration-, time- and temperature-dependent gelling (polymerization) can be attributed presumably to the changes in orientation of the —OH groups in the molecule.

The resulting primycin gel is completely translucent, stable, and does not change upon adding more solvent thereto. This favourable association property of water soluble primycin enables one to apply polymerized gels or freeze-dried membranes in therapeutical fields where the high local active agent concentration is of essential importance. Utilizing this gel-forming property of water soluble primycin, colloidal pharmaceutical compositions with highly variable active agent content can be prepared very easily without applying any particular gelling agent. The use of ethanol, admixed so far with water insoluble primycin preparations in order to attain a higher active agent content, can also be avoided, thus the unwanted side effects of ethanol can be eliminated.

In a first approach, primycin prepared according to the invention differs from the starting substance only in water solubility. However, owing to the changes in solvation properties, the association conditions and the so-called heterogeneity ratios may change as well, whereupon primycin (which is a multicomponent mixture) becomes more accessible for subsequent treatments. This is the reason why we have succeeded to obtain a two-component mixture and two separate single biologically active components by a relatively quick and well reproducible chromatographic operation.

To prepare a mixture of primycin components of formulae (A$_1$) and (A$_3$), water soluble primycin prepared according to the invention is applied as starting substance. Chromatography is performed on a silica gel column.

The preferred conditions for column chromatography are as follows: Kieselgel 60 (particle size: 0.063–0.2 mm or 0.02–0.5 mm) is applied as adsorbent. The gel is washed several times with deionized water, the aqueous phase is decanted, and the resulting gel suspension is rendered bubble-free in vacuo. A Pharmacia column (2.6×230 cm) equipped with a flow adapter is applied as chromatographic column. The continuous through-flow is maintained by a Gilson Mini-plus-2 four-channel peristaltic pump. A Gilson equipment for liquid chromatography, comprising a Holochrome Model M differential spectrophotometer, a Model 201 fraction collector and a Model $N_2$ two-channel servopotentiometric recorder, is applied to collect the fractions and to monitor the course of chromatography continuously. Water soluble primycin is applied onto the column as a 5–10 mg/ml aqueous solution. The chromatographic peaks are shown in FIG. 3.

First the column is eluted (washed) with water whereupon a substantial part of the minor components of primycin (fraction "A" in FIG. 3) can be removed. The individual peak fractions are checked by thin layer chromatography utilizing Merck DC Alufolien or DC Plastikfolien Kieselgel 60 $F_{254}$ as chromatographic plate, the upper phase of a 38:2:10:50 v/v mixture of n-butanol, ethanol, acetic acid and water as solvent (Partridge mixture), and vanillin and sulfuric acid at 105° C. as detecting agent.

The substance bound to the column, which is a mixture of the components of formulae ($A_1$) and ($A_3$), is eluted then with a 1% aqueous solution of Partridge mixture referred to above. As it appears from FIG. 3, the residual minor components are eluted first, then a pure mixture of compounds of formulae ($A_1$) and ($A_3$) is eluted, and then at the descendent stage of the elutiogram a contaminating substance with higher $R_f$ value (referred to as component "B" in the patent specifications cited above) is eluted.

The peak fractions are pooled, evaporated, gradually dehydrated utilizing distilled methanol and then absolute methanol, and then a mixture of absolute ether and acetone is added to the resulting concentrate to precipitate the product. The precipitated product is a mixture of compounds of formulae ($A_1$) and ($A_3$); this mixture is a water soluble, biologically active product. It is obtained generally with a yield of 50–60% calculated for the starting water soluble primycin. The two-component mixture melts at 165°–168° C.

In the following we have attempted to separate the compounds of formulae ($A_1$) and ($A_3$) in pure state from their mixture. Our previous investigations have shown that the adsorption characteristics of these two major components are almost the same, thus their complete separation appeared to be a lengthy and sophisticated operation involving a considerable material loss.

In our research work directed to investigate the mechanism of effect of primycin we have always attributed an essential importance to the changes in charge structure of the molecule. Any change in charge structure may basically modify (1) the membrane orientation of primycin molecule (namely only a discrete orientation may ensure e.g. the separation of antibacterial and toxic effects) and (2) the adsorption properties of the molecule or of the individual components of primycin.

Our previous gel chromatographic tests performed with water soluble primycin on Sephadex LH-20 have indicated that a change in polarity and association conditions may considerably influence the heterogeneity of primycin. In other words, the ratio of the individual components present in the peak fractions depends on the dielectric properties of the solvent system applied. Based on these observations we have attempted to separate the individual components of the mixture obtained as described above by ion exchange chromatography. A preferred method, resulting in a complete separation of the components of formulae ($A_1$) and ($A_3$), is given below.

The water soluble mixture of the components of formulae ($A_1$) and ($A_3$), prepared as described above, is applied as starting substance. A 4–5 mg/ml aqueous solution of this two-component mixture is applied onto a carboxymethyl cellulose column in $NH_4^+$ cycle (Whatman CM-52 cellulose, preswollen). A Pharmacia K-26 column (2.6×5 cm) equipped with a flow adapter is utilized as column. The conditions of chromatography and the elutiogram are given in FIG. 4.

The column is washed first with water to remove the residual minor components ("A"), and then elution is continued with a 5–8 molar aqueous ammonium hydrocarbonate solution to obtain the pure component of formula ($A_3$). The component of formula ($A_1$) remains bound to the column. The ammonium hydrocarbonate effluents are pooled, a small amount of n-butanol (antifoaming agent) is added, and the mixture is evaporated to almost dryness. Washing with water and evaporation is repeated several times to remove ammonium hydrocarbonate, thereafter the residue is completely dehydrated by evaporating first distilled methanol and then absolute methanol from the residue. The resulting concentrate is treated with absolute ether to precipitate the product, the separated solid is filtered off and washed with a small amount of dry acetone.

The resulting solid melts at 159°–61° C. and is obtained with a yield of about 45–50% calculated for the starting two-component mixture. The water solubility of the resulting substance is about 2–6 mg/ml. The decrease in melting point (that of the starting mixture is 165°–168° C.) and in water solubility (that of the starting mixture is 40–60 mg/ml) can be attributed to the presence of minor amounts of bound $NH_4^+$ and of ammonium hydrocarbonate contaminations.

To remove these contaminations the resulting substance is dissolved in water, the solution is applied onto a carboxymethyl cellulose column in $H^+$ cycle, the column is fully washed with water, and then gradually dehydrated first with distilled methanol and then with absolute methanol. Thereafter the substance is eluted with absolute methanol comprising 10 mmoles of acetic acid. The effluent is evaporated to a small volume, absolute methanol is added to the concentrate and evaporation is repeated several times, and then the product is precipitated from the concentrate with absolute acetone. The separated substance is filtered through a G4 sintered glass filter, washed repeatedly with acetone and dried.

In this way a compound of formula ($A_3$) is obtained in pure state, melting at 164°–166° C. (FIG. 13). The water solubility of the compound of formula ($A_3$) is about 50 mg/ml. The repeated ion exchange chromatography runs with a material loss of maximum 10%.

The second component of the starting two-component mixture, i.e. the compound of formula ($A_1$), which remains bound to the CM-52 carboxymethyl cellulose column in $NH_4^+$ cycle after eluting it with aqueous ammonium hydrocarbonate, is separated as follows:

The column is washed with water to remove ammonium hydrocarbonate completely, and then gradually dehydrated first with distilled methanol and then with absolute methanol. The bound substance is eluted then with absolute methanol comprising 10 mmoles of acetic acid. The effluent is evaporated to a small volume, absolute methanol is added to the concentrate and evaporation is repeated several times to remove acetic acid, and then absolute acetone is added to the concentrate to precipitate the product.

In this way the component of formula ($A_1$) is obtained as a pure solid melting at 167°–168° C. (FIG. 12). The compound is well soluble in water. No subsequent ion exchange chromatography is required to purify this component, since in the acetic acid elution step the residual and "bound" $NH_4^+$ as well as any ammonium hydrocarbonate present are eluted as ammonium acetate, and this compound remains dissolved in the acetone precipitation step.

Thus, starting from a water insoluble primycin, according to the invention a water insoluble primycin is prepared, from which, if desired, a water soluble mixture of the components of formulae ($A_3$) and ($A_1$) can be prepared, and the individual components of this two-component mixture can also be separated. All of the products prepared according to the invention are water soluble and biologically active.

Figure 5:
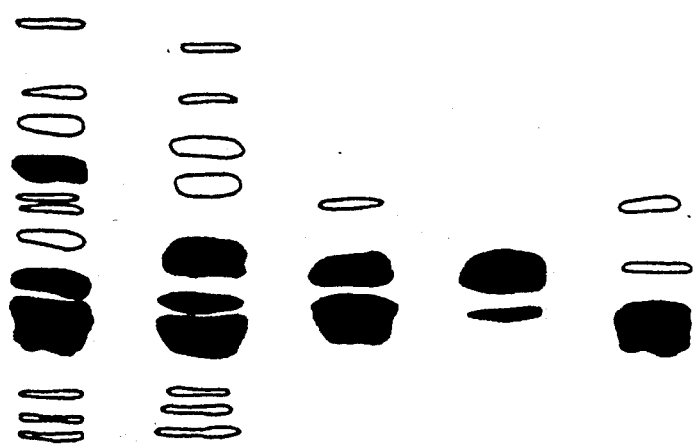
FIG. 5. Thin layer chromatography of primycin components.

The comparative thin layer chromatograms and the results of biological evaluation are shown in FIG. 5. Thin layer chromatography was performed on a Kieselgel 60 DC Alufolien $F_{254}$ plate utilizing the upper phase of a 38:2:10:50 v/v mixture of butanol, ethanol, acetic acid and water as solvent and a mixture of vanillin and sulfuric acid at 105° C. as detecting agent. Biological evaluation was performed by agar diffusion test on *Bacillus subtilis*. The minimum inhibiting concentrations (MIC) measured in biological evaluation are summarized in Table II below.

TABLE II

| | MIC μg/ml |
|---|---|
| Starting water insoluble primycin | 0.04–0.06 |
| Water soluble primycin | 0.08–0.2 |
| A mixture of ($A_1$) and ($A_3$) | 0.05–0.1 |

TABLE II-continued

| | MIC μg/ml |
|---|---|
| Compound of formula ($A_3$) | 0.5–1.0 |
| Compound of formula ($A_1$) | 0.03–0.06 |

The results of biological evaluation indicate that the individual components of primycin are different in activity. This difference in activity can be attributed presumably to the fact that the individual components exert their antibacterial effects in different ways, or may have different points of attack when acting on the living organism. This explains the fact that a single component is able to synergize the effect of another component (see e.g. Hungarian patent No. 196,309).

The gelling properties of the individual components of formulae ($A_1$) and ($A_3$) and those of the two-component mixture have also been examined. It has been found that when the concentration is maintained at a constant value, the gelling rate decreases. The 5–10 mg/ml aqueous solutions of the single components can be stored for days (maximum for one week) without any observable change, whereas an aqueous solution of the two-component mixture of the same concentration gellifies within 1–2 days, and the gelling time of water soluble primycin in the same concentration is shorter/than one day. It can be assumed that this delay in gelling is connected with a change in conformation or with the orientation of the hydroxy groups.

It is known from previous publications that primycin is highly sensitive to electrolytes. In harmony with this observation, which is also in harmony with the ionophoric nature of primycin, we have observed that in water soluble primycin the orientation of hydroxy groups can be reverted with cations, which results in an abrupt but reversible decrease in water solubility of primycin. However, when stored in a sugar solution of appropriate concentration (such as in isotonic glucose solution) both the polymerization and the cation sensitivity of primycin can be suppressed to a great extent.

$^{13}C$ NMR spectra of the products prepared according to the invention are presented in FIGS. 6 to 11.

Figure 6:
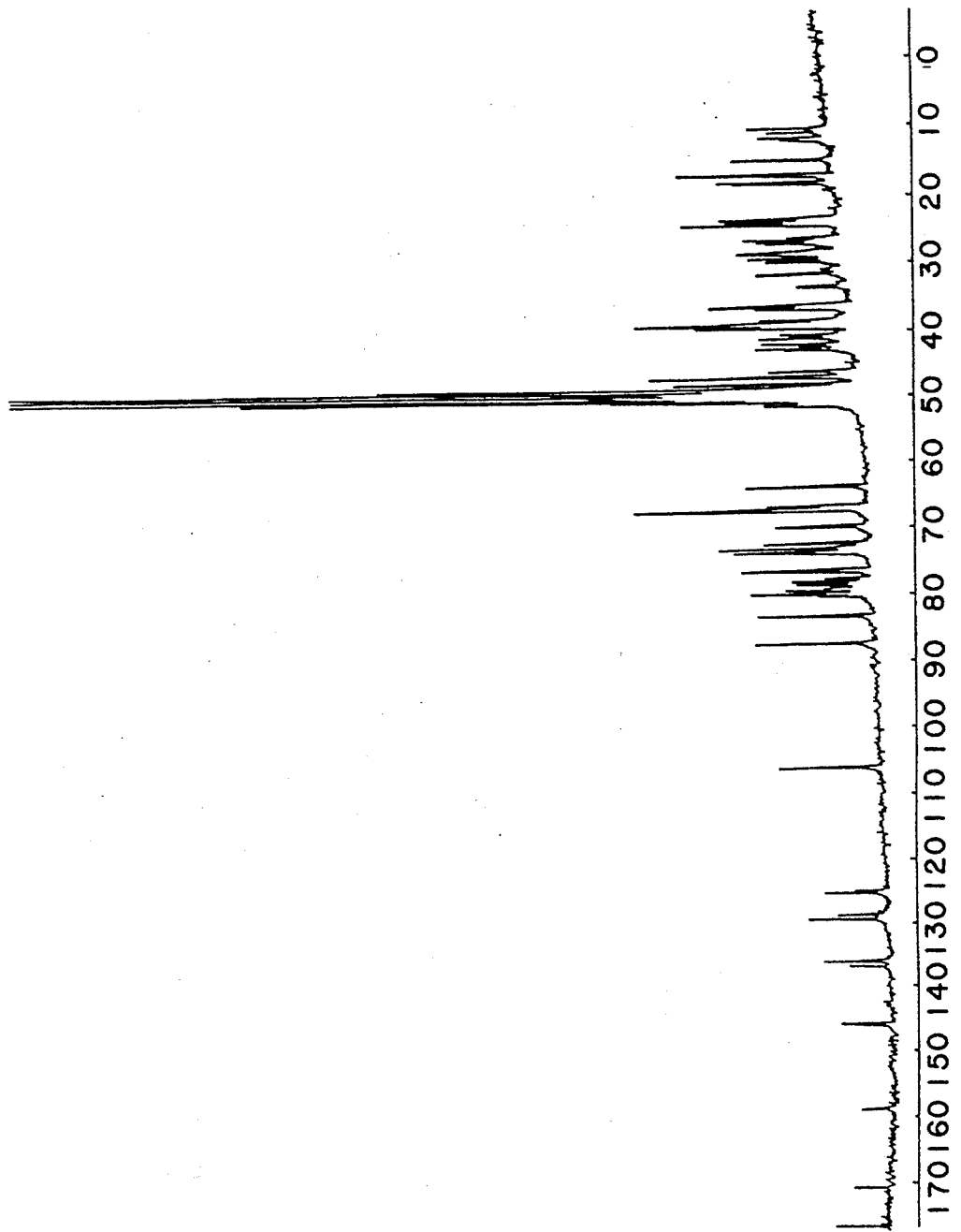
FIG. 6. Normal $^{13}C$ NMR spectrum of water-soluble primycin.

FIG. 6 shows the normal $^{13}C$ NMR spectrum of water soluble primycin (c=500 mg/400 μl of methanol-$d_4$, T=323K).

Figure 7:
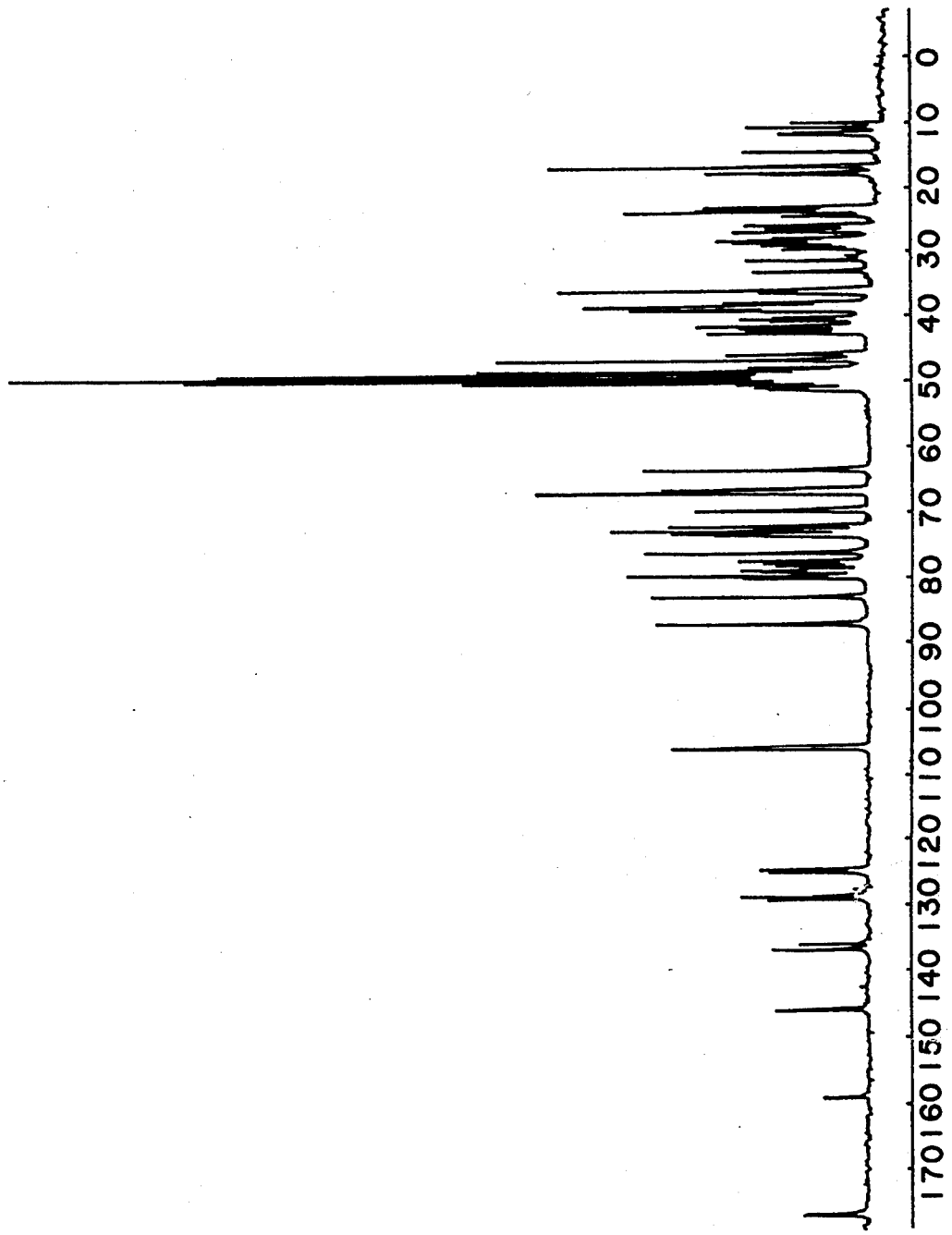
FIG. 7. Normal, proton-decoupled $^{13}C$ NMR spectrum of the mixture of primycin components ($A_1$) and ($A_3$).

FIG. 7 shows the normal, proton-decoupled $^{13}C$ NMR spectrum of the two-component mixture of components of formulae ($A_1$) and ($A_3$) (c=250 mg/1.5 ml of methanol-$d_4$, T=323K, NS=3000).

Figure 8:
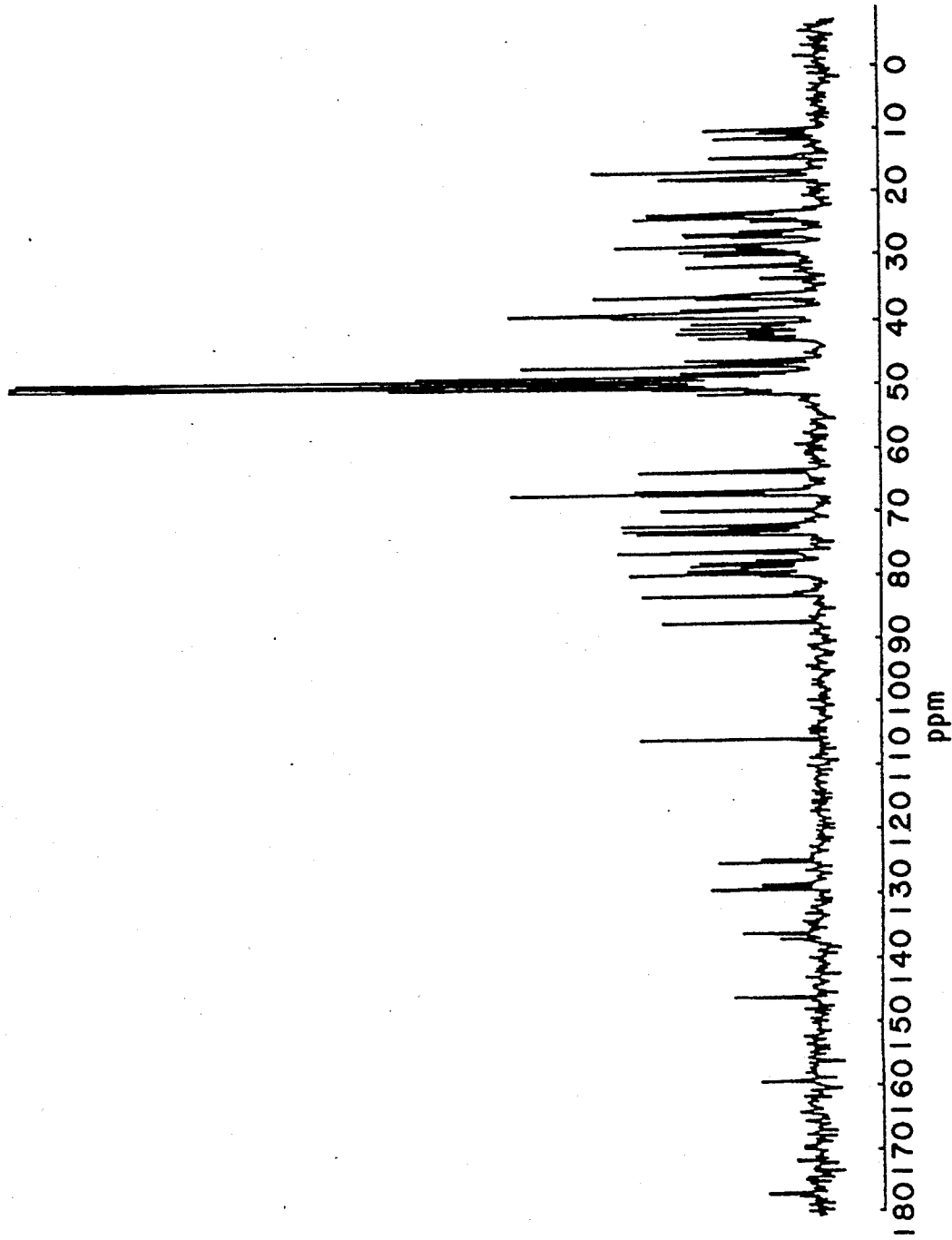
FIG. 8. Normal, proton-decoupled $^{13}C$ NMR spectrum of primycin component ($A_3$).

FIG. 8 shows the normal, proton-decoupled $^{13}C$ NMR spectrum of the compound of formula ($A_3$) (c=100 mg/400 μof methanol-$d_4$, T=323K, NS=5000).

Figure 9:
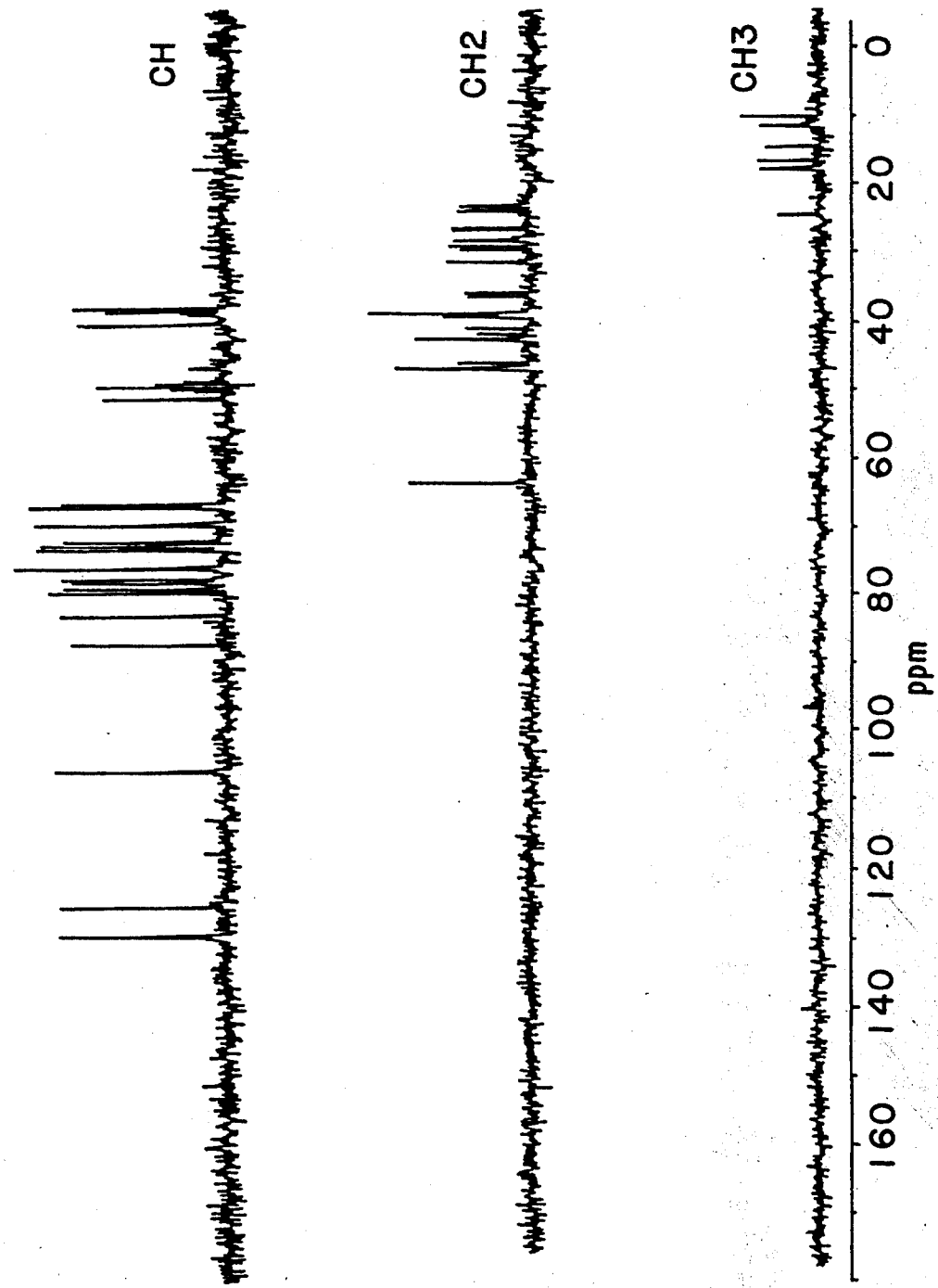
FIG. 9. $^{13}C$ NMR spectrum of the ammonium acetate-containing compound of formula ($A_3$).

FIG. 9 shows the $^{13}C$ NMR spectrum of the ammonium acetate-containing compound of formula ($A_3$); the spectrum was constructed utilizing EPT pulse frequency (c=50 mg/400 μl of methanol-$d_4$, T=323K, NS=2000).

Figure 10:
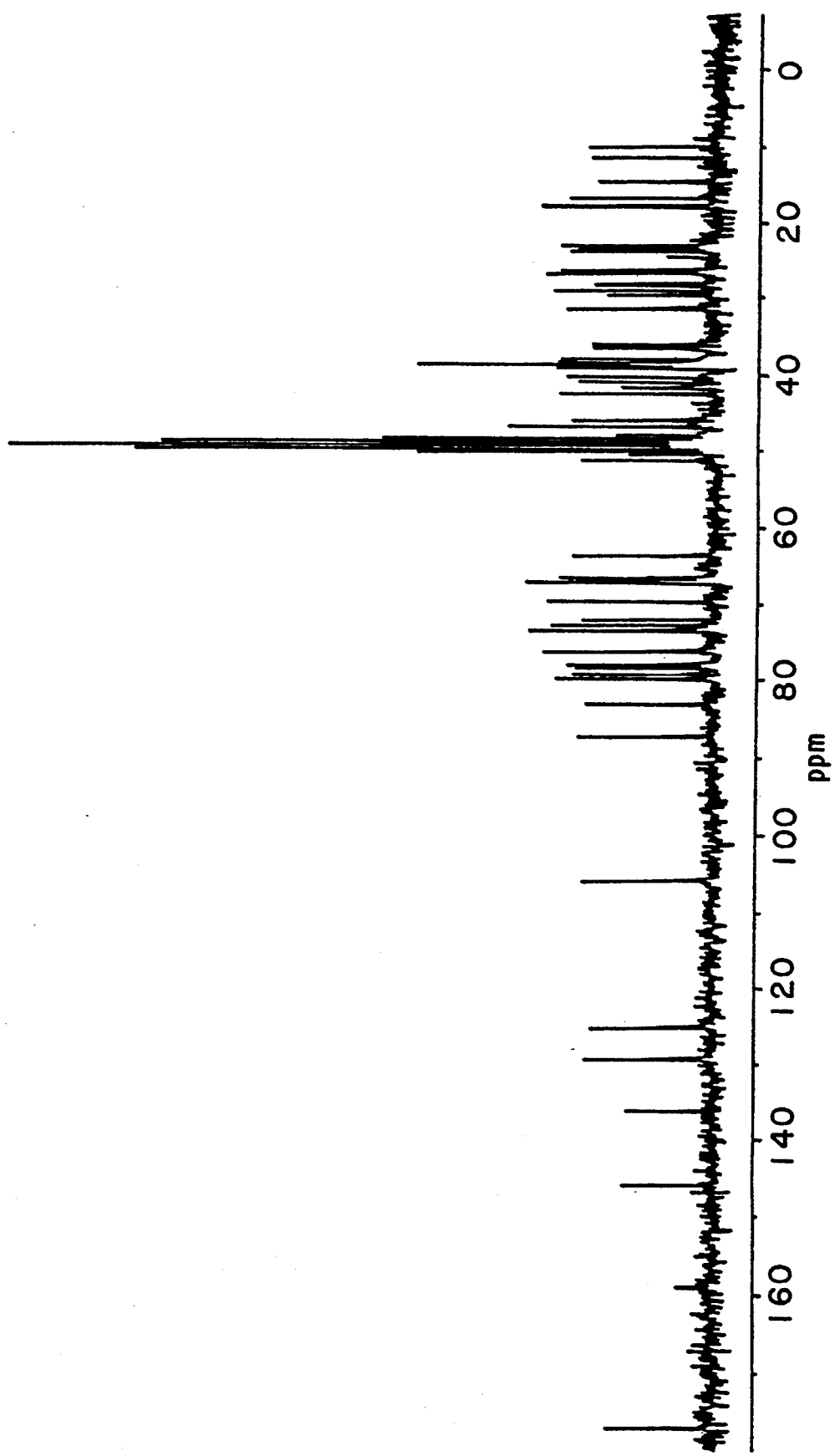
FIG. 10. Normal, proton-decoupled $^{13}C$ NMR spectrum of the ammonium acetate-containing compound of formula ($A_3$).

FIG. 10 shows the normal, proton-decoupled $^{13}C$ NMR spectrum of the ammonium acetate-containing compound of formula ($A_3$) (c=50 mg/400 μl of methanol-$d_4$, T=323K, NS=2700).

Figure 11:
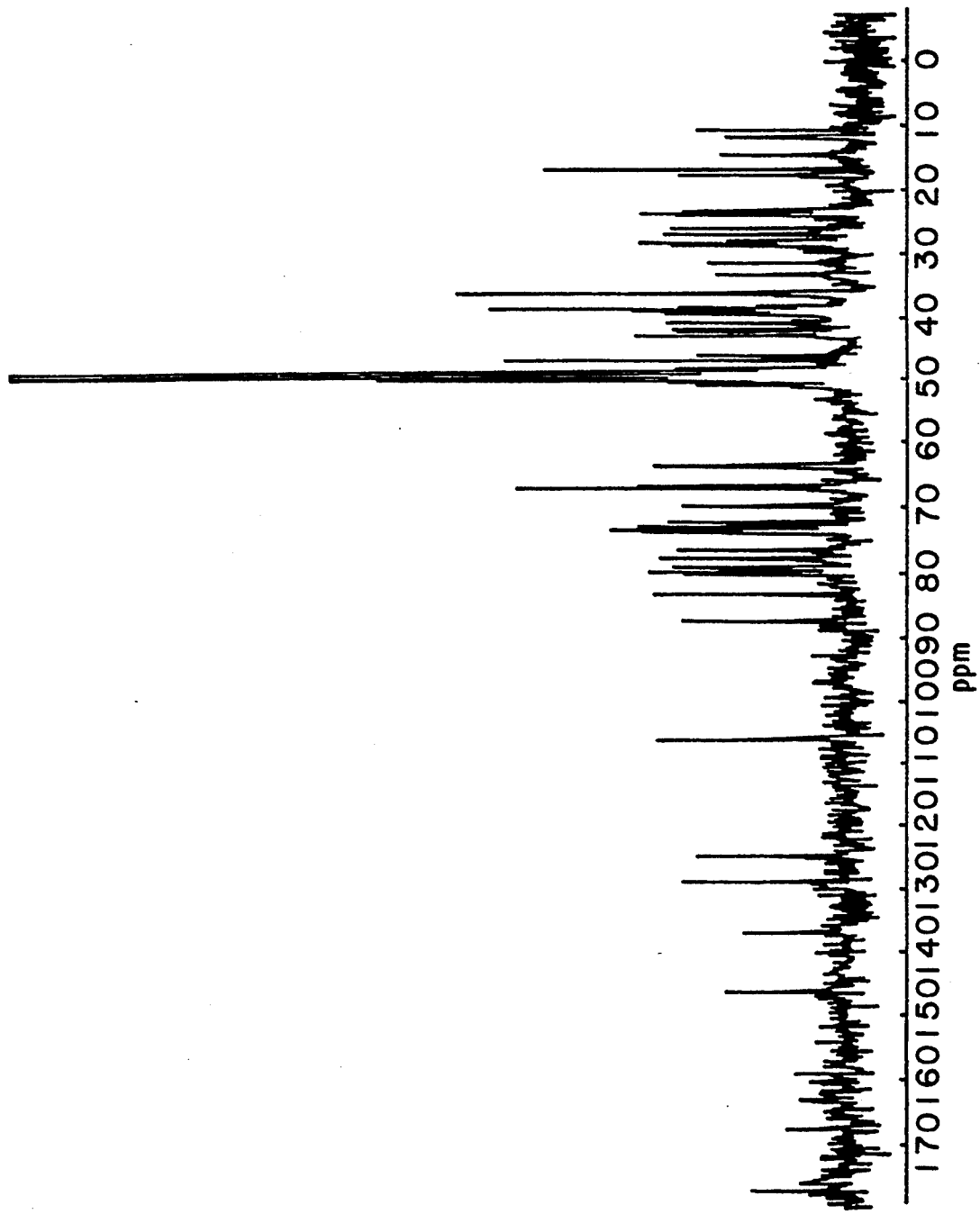
FIG. 11. Normal, proton-decoupled $^{13}C$ NMR spectrum of compound of the formula ($A_1$).
Figure 12:
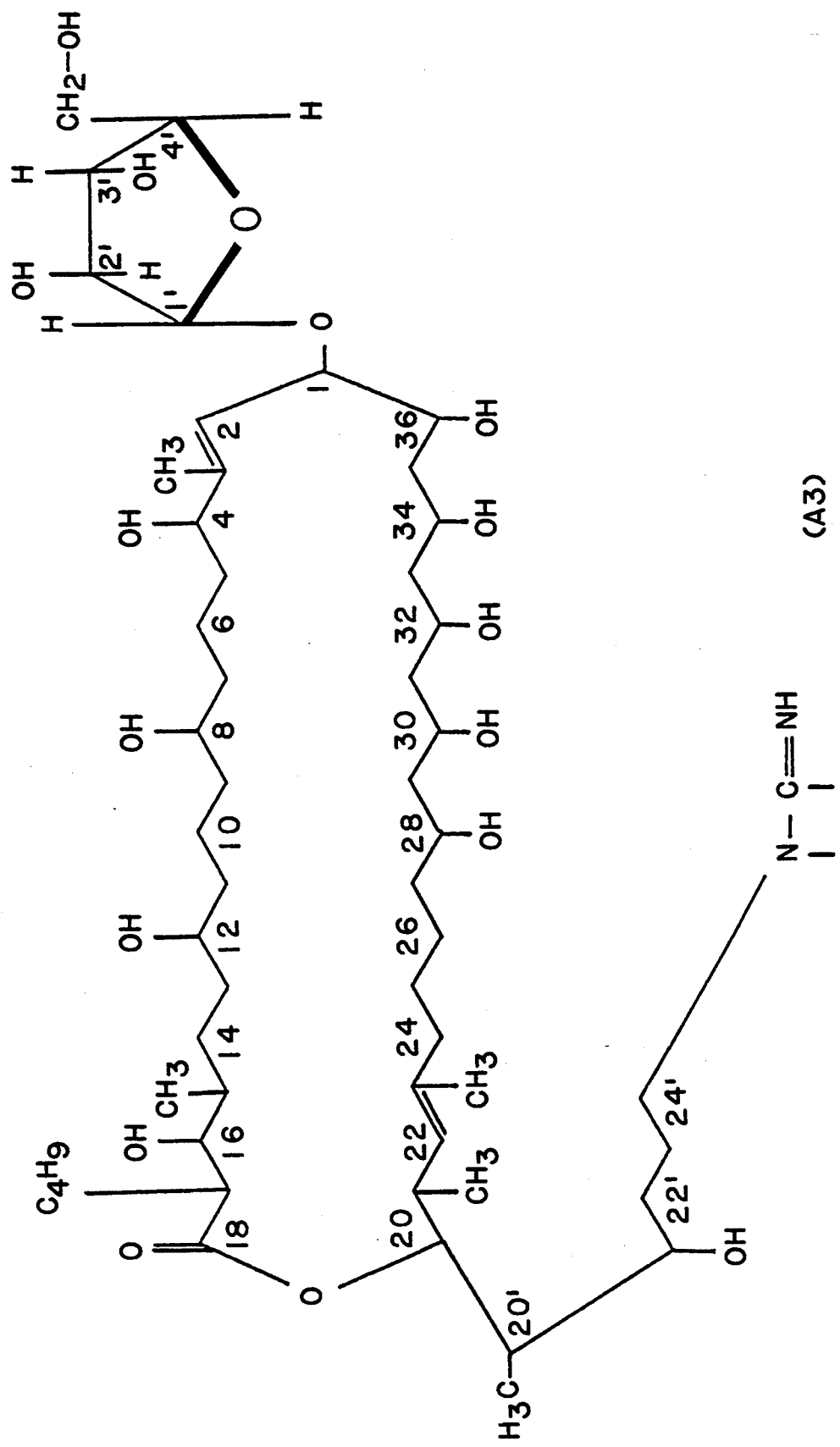
FIG. 12. Compound of formula ($A_1$).
Figure 13:
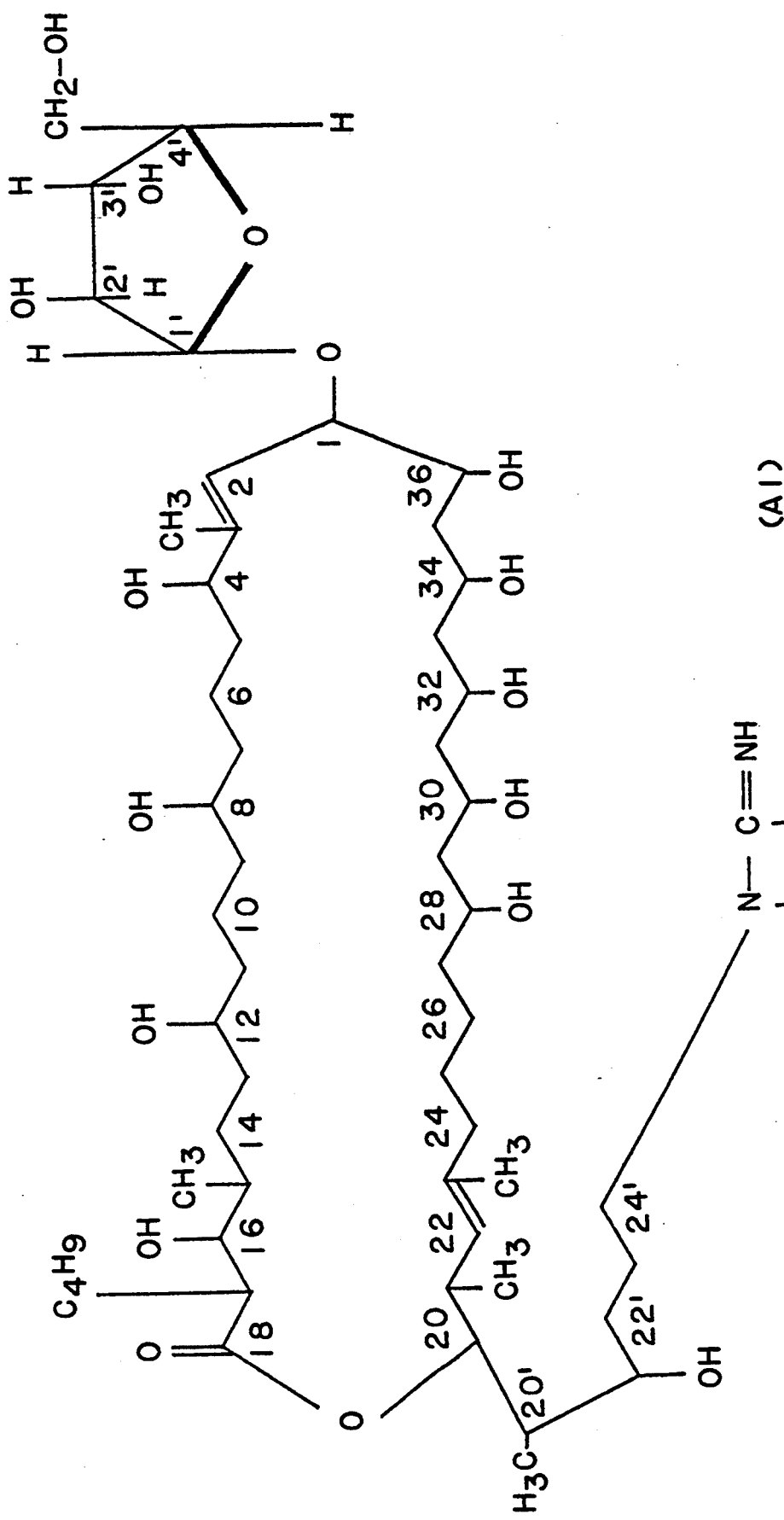
FIG. 13. Compound of formula ($A_3$).

FIG. 11 shows the normal, proton-decoupled $^{13}C$ NMR spectrum of the compound of formula ($A_1$) (c=80 mg/400 μl of methanol-$d_4$, T=323K, NS=2700).

From the spectral data the following conclusions can be drawn:

No ring closure proceeds in the reaction applied to prepare water soluble primycin. It is unambiguous on the basis of the $^{13}C$ NMR spectrum that the molecule examined contains four quaternary carbon atoms. The signal of carbonyl carbon appears at 176.7 ppm. The signal of the quaternary carbon atom in the guanidine group appears at 158.8 ppm, whereas the signals of the remaining two quaternary carbon atoms appear at 145.7 and 135.8 ppm, respectively (FIG. 6). If a ring closure had proceeded, two additional quaternary carbon atoms would have appeared in the NMR spectrum.

According to the NMR spectra it is highly probable that an intermediate is formed in the quasi condensation reaction (FIG. 6, signal at 170.4 ppm which may be the signal of a quaternary carbonyl). This signal appears only if the water soluble primycin is separated from anhydrous (absolute) solvents. Primycin is chromatographed then in an aqueous medium, whereupon the signal at 170.4 ppm disappears (see FIG. 7, the NMR spectrum of the two-component mixture). This may reveal that the supposed intermediate undergoes hydrolysis or selective adsorption, both resulting in its disappearance.

In the following, on the basis of $^{13}C$ NMR spectrum construction (DEPT) and utilizing J-modulated spin-echo technique, the number of carbon atoms of different orders (quaternary, tertiary /CH/, secondary /CH$_2$/ and primary /CH$_3$/) has been determined in the major components. According to this determination the molecule contains four quaternary carbon atoms corresponding to the signals discussed above, 22 tertiary carbon atoms (the signal at 105.6 ppm corresponds to the anomeric carbon of arabinose and the signals at 129.1 and 124.9 ppm correspond to the tertiary carbon atoms of the two unsaturated bonds), 22–23 secondary carbon atoms (the uncertainty can be attributed to the accidental coincidence of the signals of methylene carbons in similar chemical environments) and 6 primary carbon atoms.

From the above it follows that the empirical formulae of the major components of water soluble primycin are practically identical with those discussed in the literature. In the NMR spectrum of water soluble primycin the signals of two epimers can be distinguished which, owing to the different sterical configurations of —OH, —CH$_3$ and butyl groups, appear as doublets.

—OH groups appear at positions 4, 8, 12, 16, 28, 30, 32, 34, 36 and 21' of the molecule;
—CH$_3$ groups appear at positions 3, 15, 21, 23 and 20' of the molecule, and
the n-butyl group appears at position 17 of the molecule.

The $^{13}C$ NMR spectrum of the two-component mixture prepared according to the invention is shown in FIG. 7.

Comparing FIGS. 6 and 7 it can be stated that the weight ratios of the major components change; water soluble primycin contains the compound of formula (A$_3$) in the greater amount (see FIG. 6), whereas in the two-component mixture the compound of formula (A$_1$) is the dominant one. This is in good agreement with the results of thin layer chromatography shown in FIG. 5.

From the $^{13}C$ NMR spectra shown in FIGS. 10 and 11 it follows that the number of carbon atoms present in the two major components of formulae (A$_3$) and (A$_1$) are practically the same, with the proviso that due to the uncertainties discussed above the number of secondary (CH$_2$) carbon atoms may differ by one.

The small, sometimes negligible differences in chemical shifts of the carbon atoms in identical positions in the two major components may indicate that there is no significant difference between the two major components; perhaps a conformational difference or a monomer-dimer interaction may appear (FIG. 8).

The details of the invention (materials and methods) and the examples illustrating the invention are given below.

Materials and methods

All of the solvents and chemicals utilized in the examples were fine chemicals of the highest analytical purity (produced by Merck, Fluka, Reanal, Whatman, Macherey-Nagel Co., Sigma). Some of the solvents were purified or re-purified (rendered absolute) by us. The dry solvents were stored over a molecular sieve (pore diameter: 3–4 Å).

The following substances were applied as adsorbents for column chromatography:
Kieselgel 60 (particle size: 0.062–0.2 mm or 0.2–0.5 mm), carboxymethyl cellulose MN 2100 CM (Macherey-Nagel), CM-52, preswollen, microgranular (Whatman).

The following substances were applied as adsorbents in thin layer chromatography:
DC Alufolien Kieselgel 60 F$_{254}$ 20×20 cm/0.2 mm (Merck No. 5554),
DC Plastikfolien Kieselgel 60 F$_{254}$ 20×20 cm/0.2 mm (Merck No. 5735),
Polygram Sil. G/UV$_{254}$ 20×20 cm/0.25 mm (Macherey-Nagel).

Liquid chromatography was performed on a Gilson Medical Electronics apparatus equipped with a differential spectrophotometer (Holochrome HM type UV monitor), with a Model 201 fraction collector, with a Model N$_2$ recording unit and with a Minipuls-2 peristaltic pump.

The thin layer chromatograms were detected with a modified vanillin—sulfuric acid reagent. 250 mg of vanillin (pro anal. quality) were dissolved in 100 ml of absolute ethanol, the solution was cooled to $-10°$ C., and 2.5 ml of cc. sulfuric acid were added dropwise. The solution was sprayed onto the plate (utilizing nitrogen as propellant) or the plate was immersed into the reagent solution. The plates were dried in cold air stream and then activated at 105° C. for 1–2 minutes.

Sakaguchi reaction was performed in two ways:
(i) The appropriately dried plates were treated without heating with a 0.2% acetone solution of 8-hydroxyquinoline, the plates were dried in cold air stream, then a 0.5N sodium hydroxide solution comprising 0.2% of bromine was sprayed onto the plates, and the plates were dried without heating.
(ii) 2.5 g of sodium hydroxide were dissolved in 5 ml of water. The solution was cooled to 2°–5° C., diluted with 45 ml of pre-cooled methanol, filtered, and 50 mg of 8-hydroxyquinoline were dissolved in the filtrate. The resulting solution was the first reagent mixture. The second reagent mixture was prepared by dissolving 250 mg of N-bromosuccinimide in 50 ml of 10% aqueous ethanol cooled to 2°–5° C. The plates were treated with the reagent mixtures as described in point (i) above.

Sakaguchi reaction was also applied to detect primycin in solutions. In these examinations the microchemical method discussed in the literature was applied with the following modifications: The measurements were performed with N-bromosuccinimide. The standard serial dilution was made on arginine, and the developed colour density was measured on an Opton spectrophotometer at 520 nm. The following reactants were applied always in freshly prepared forms:
(1) 0.01% alkaline α-naphthol solution (prepared by diluting a 0.2% ethanolic solution of α-naphthol with a 10% aqueous sodium hydroxide solution),
(2) 0.45% N-bromosuccinimide (NBS) solution in 10% aqueous ethanol, and
(3) 40% aqueous urea solution.

The determinations were performed at 0° C. In contrast to the literature data, the volume of the reaction mixture was 1.7 ml, and the reaction mixture consisted of the following components:

| solution to be examined | ml |
|---|---|
| alkaline α-naphthol solution | 0.4 ml |
| NBS reagent solution | 0.1 ml |
| urea solution | 0.2 ml |

It is well known that Sakaguchi reaction is very sensitive to various alcohols and in general to oxo compounds. Thus e.g. with primycin even an alcohol (methanol, ethanol) content of 20% results in a considerable decrease of extinction measured at 520 nm. This decrease is, however, not connected with the developed colour density but with its spectral shift (shift to the lower wavelength range). If primycin is not dissolved in pure water but in an organic solvent or in an organic solvent mixture (such as in a 1:1:2 v/v mixture of butanol, ethanol and water), the characteristic coloured product developed upon the Sakaguchi reaction can be quantitatively extracted into the butanol phase; the absorption maximum of the colour in this phase is at 480 nm.

Agar diffusion technique was applied for the biological evaluation of primycin. As test organism *Bacillus subtilis* ATCC 6633 was applied.

*Bacillus subtilis* ATCC 6633 was cultivated on a Schaeffer medium (Nutrient Broth No. 2/oxoid) with the following composition:

| beef extract | 3.2 g |
|---|---|
| peptone | 3.2 g |
| NaCl | 1.6 g |
| $MgSO_4.7H_2O$ | 0.25 g |
| KCl | 1.0 g |
| $FeSO_4.7H_2O$ | 278 μg ($10^{-6}$ mole) | dissolved in 900 ml of water

The solution was heated in a pressurized vessel for 30 minutes at a pressure of 1.5 atmospheres, thereafter the pE was adjusted to 7.0–7.2 with 5–6 drops of 10N sodium hydroxide solution, 90 ml portions of the solution were poured into cultivating dishes, and the portions were supplemented with 10 ml, each, of the following solutions:
a) 236 mg ($10^{-3}$ mole) of $Ca(NO_3)_2 \cdot 4H_2O$ dissolved in 100 ml of distilled water, and
b) 1979 mg ($10^{-5}$ mole) of $MnCl_2.4H_2O$ dissolved in 100 ml of distilled water.

The titrating nutrient medium was prepared as follows:

5 g of meat extract (Beef Extract Difco), 0.5 g of peptone (Bacto Peptone Difco), 1 g of $Na_2HPO_4$ and 0.1 g of $KH_2PO_4$ were dissolved in 100 ml of distilled water, the solution was boiled for 2 hours, and then the pH was adjusted to 8. The warm solution was filtered, allowed to cool, the filtrate was diluted with 900 ml of distilled water, and 20 g of agar (Bacto Agar Difco), dissolved in a Koch pot, were added to 1 liter of the solution. The pH of the warm solution was checked. 100 ml portions of the resulting solution were filled into storage flasks and then heat treated for 20 minutes in a pressurized vessel under a pressure of 1.5 atmospheres.

The titrating plates were prepared from the above nutrient medium as follows: 100 ml of the nutrient medium were melted on a water bath, the melt was cooled to 40°–50° C., and 0.5 ml of a spore suspension of *Bacillus subtilis* ATCC 6633 was admixed cautiously with the still liquid nutrient medium. The inoculated nutrient medium was filled into a glass tray of 30×30×3 cm dimensions, made of 3–4 mm thick glass plates, the solidified agar plate was pre-incubated at 37° C. for 0.5–1 hour, and then 42 holes of 10 mm diameter were cut into the plate.

Solutions containing 20–50 /ug/ml of active agent were prepared from the substances to be examined [starting water insoluble primycin; water soluble primycin; a mixture of the compounds of formulae ($A_1$) and ($A_3$); a compound of formula ($A_1$); a compound of formula ($A_3$)] in water or in a 1:1:2 v/v mixture of butanol, ethanol and water, and the resulting solutions were diluted with buffered distilled water (0.15 molar phosphate buffer, pH=7.6) to concentrations of 0.05–0.1, 0.5–1.0 and 2.0 /ug/ml. 0.1 ml portions of the resulting solutions were filled into the holes of the titrating agar plates, and the agar plates were incubated in a thermostate at 37° C. for 18–20 hours. Thereafter the diameters of the diffusive extinction zones were measured in mm, the obtained values were plotted on a semi-logarithmic scale against the concentrations of the standard serial dilutions, and the activity values were determined by extrapolation.

EXAMPLE 1

Preparation of Water Soluble Primycin 500 mg (0.46 mmole) of finely powdered primycin (contaminated with lead) and 100 ml of absolute ethanol were filled into a round-bottomed flask of 250 ml capacity. The flask was attached to a reflux condenser fitted with a drying tube filled with $CaCl_2$ and soda lime, and the mixture was refluxed until maximum dissolution was attained (about 15–30 minutes). Thereafter 50 μl (0.46 mmole) of ethyl cyanoacetate were added to the mixture; the reagent was washed into the flask with a small amount of absolute ethanol. The mixture was refluxed for 15 minutes, and then 25 mg (0.46 mmole) of sodium methoxide were added to the mixture in three equal portions at intervals of 30 minutes. The individual portions of the reactant were washed into the flask with 1–2 ml of distilled (96%) ethanol. Even after the introduction of the first portion of sodium methoxide the reaction mixture started getting clear, then the total amount of primycin dissolved, and the reaction mixture turned light pink. At the end of the reaction time (4 hours) the mixture was allowed to cool, filtered through a G4 sintered glass filter, and concentrated to a small volume in a Rotavapor R 110 (Büchi) apparatus. Thereafter the ethanol content of the reaction medium was gradually changed for methanol in such a way that the separated substance was dissolved in absolute methanol, the solvent was evaporated, and this operation was repeated. Upon this treatment the substance, having a limited solubility in ethanol, got highly soluble in methanol and remained dissolved even in some /milliliters of methanol. At this stage the product was precipitated from the methanolic concentrate with absolute ether. The separated substance was filtered through a G4 sintered glass filter, washed with absolute acetone, and dried in a vacuum drying pistol ("Blaugel", chloroform/ethanol, bp.: 65°-70° C.).

410 mg (82%) of water soluble primycin were obtained, its thin layer chromatogram is shown in FIG. 5. Water solubility: 50 mg/ml, m.p.: 162°-164° C., biological activity (on Bacillus subtilis): 0.08-0.2 /ug/ml.

EXAMPLE 2

Preparation of a Two-Component Mixture of the Primycin Components of Formulae ($A_1$) and ($A_3$)

The water soluble primycin prepared as described in Example 1 was applied as starting substance. The major components of primycin were separated by column chromatography on silica gel. Silica gel (Kieselgel 60, particle size: 0.2-0.5 mm) was purified by repeated washings with deionized water and decanting. Before filling in, the homogeneous suspension was rendered bubble-free in vacuo.

Figure 1:
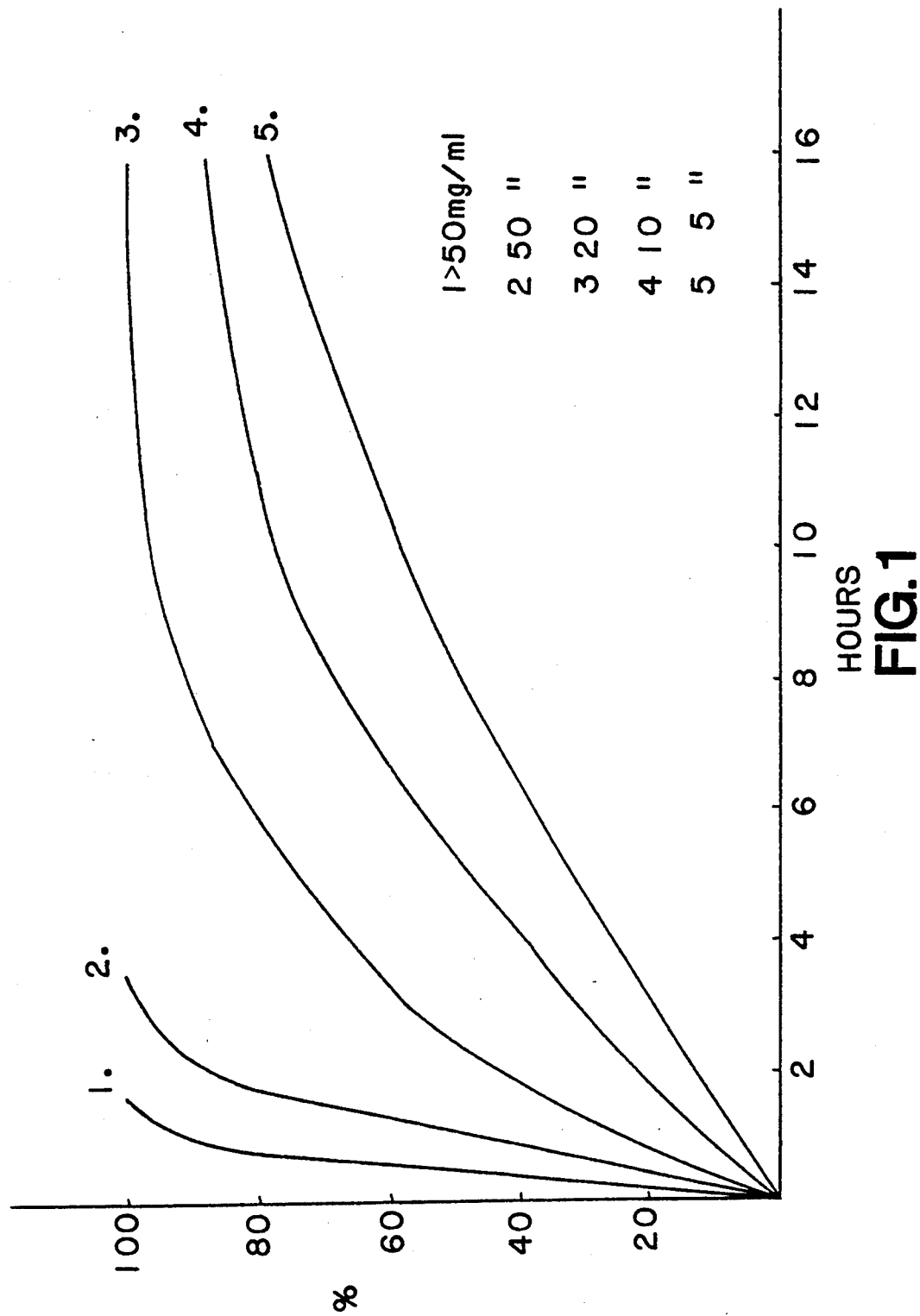
FIG. 1. Gelling process as a function of concentration and time.
Figure 2:
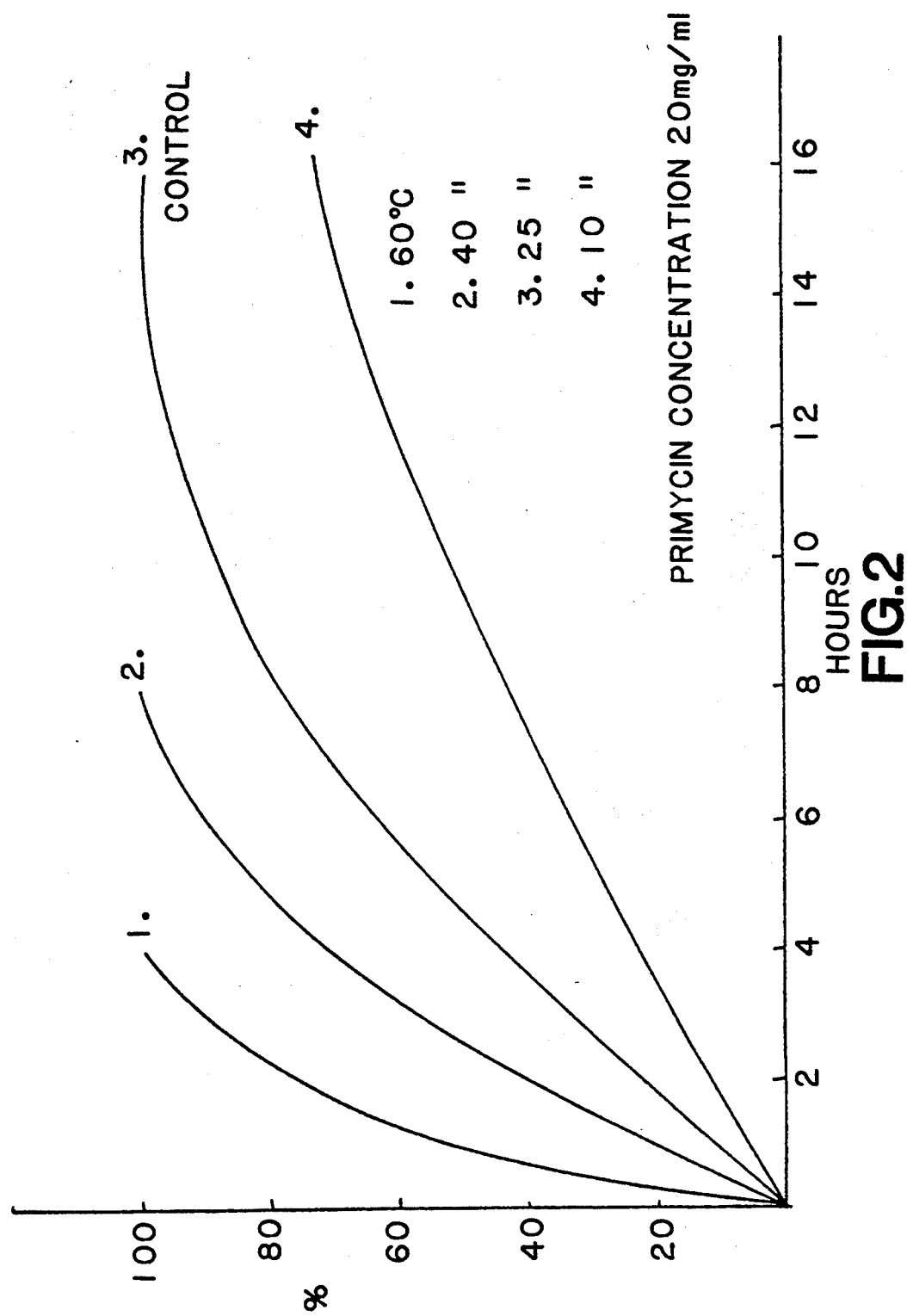
FIG. 2. Effects of temperature on gelling.
Figure 3:
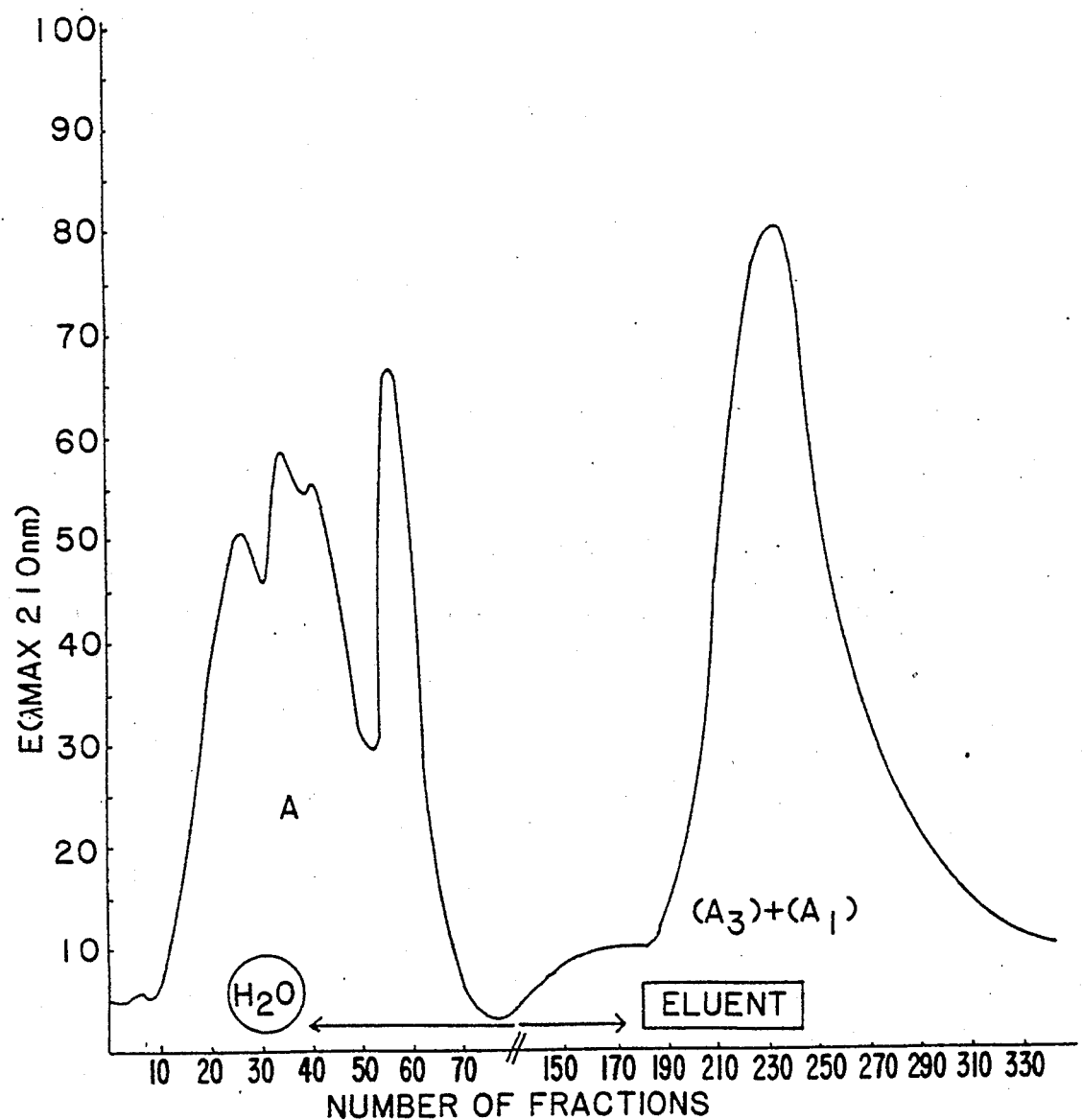
FIG. 3. Preparation of primycin components ($A_1$) and ($A_3$). Elutiogram from silica gel column.

Silica gel was filled into a Pharmacia column of 2.6×230 cm dimensions, equipped with a flow adapter. A 5-10 mg/ml aqueous solution of 500 mg of the starting substance, filtered through a G3 sintered glass filter, was continuously applied onto the column through the flow adapter. Thereafter the column was eluted with water at a rate of 130 ml/hour (=25 ml/hour/cm$^2$), and effluent fractions of 24 ml were collected. The conditions of chromatography and the elutiogram are shown in FIG. 3.

Elution was continued then with a 1% aqueous solution of Partridge mixture (Partridge mixture is the upper phase of a 38:2:10:50 v/v mixture of n-butanol, ethanol, acetic acid and water). The individual peak fractions were checked by thin layer chromatography. The peak fractions containing the two components were pooled, a small amount of n-butanol (antifoaming agent) was added, the solution was concentrated in a Rotavapor apparatus, and the concentrate was gradually dehydrated first with distilled methanol and then with absolute methanol. The resulting concentrate was treated with absolute ether, the precipitated substance was filtered off, washed with acetone and dried in a drying pistol. 260 mg (52%) of a solid substance were obtained; m.p.: 165°-168° C., solubility in water: 50 mg/ml, biological activity (on *Bacillus subtilis*): 0.05-0.1 /ug/ml.

EXAMPLE 3

Preparation of the Component of Formula ($A_3$)

Figure 4:
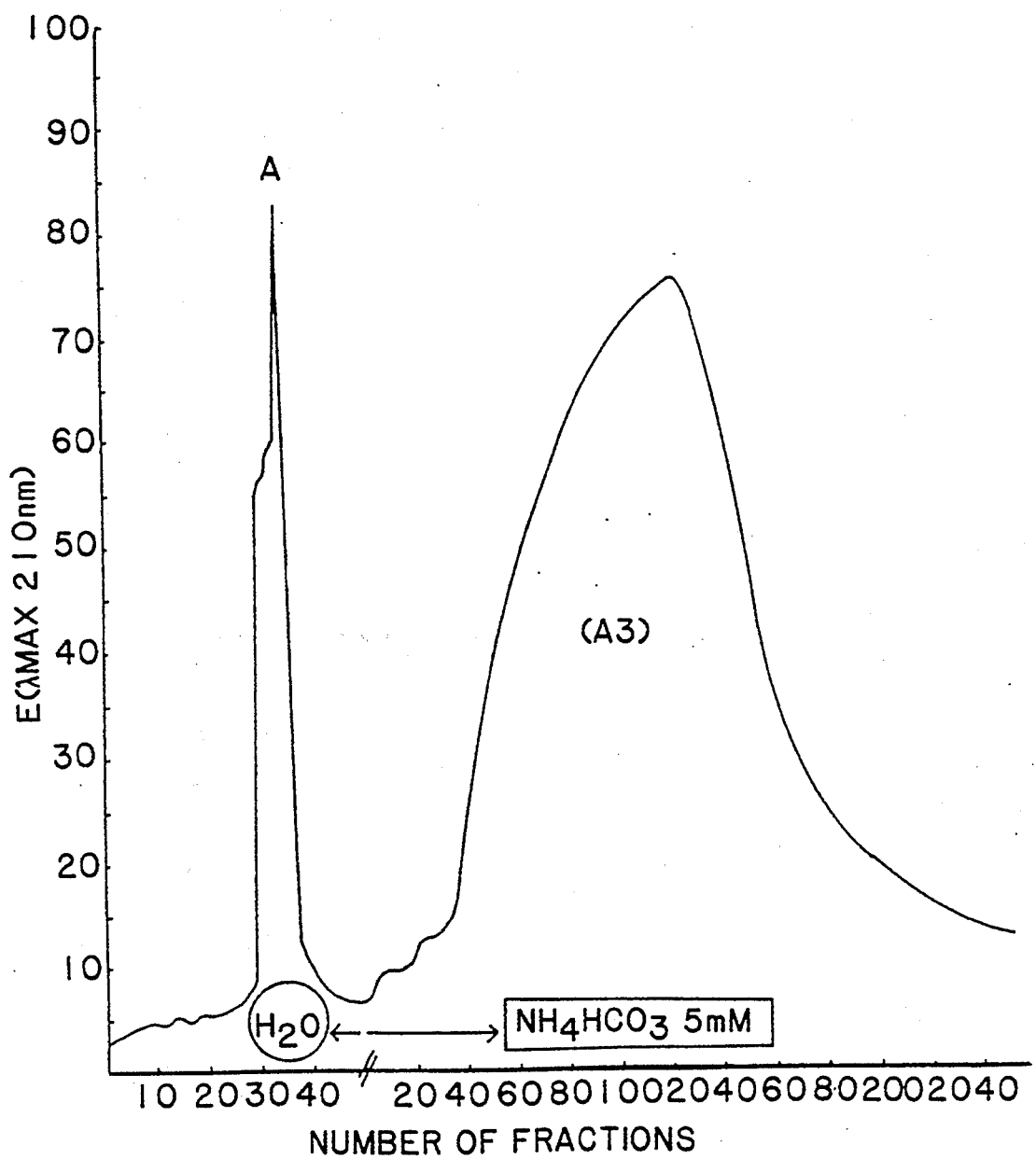
FIG. 4. Preparation of primycin component ($A_3$). Elutiogram from CM-52 cellulose column.

The two-component water soluble mixture prepared as described in Example 2 was applied as starting substance. The components were separated from one another by ion exchange chromatography on carboxymethyl cellulose in $NH_4^+$ cycle. CM-52 cellulose (preswollen, microgranular, Whatman) in $H^+$ cycle was suspended in water, treated with 1 molar aqueous ammonium hydrocarbonate solution, washed several times with water, decanted, and treated in vacuo to remove the bubbles. This absorbent was filled into a Pharmacia column (2.6×6 cm) equipped with a flow adapter. 450 mg of the starting two-component mixture were applied onto the column as a 4.5 mg/ml aqueous solution through the flow adapter. Elution was performed at a flow rate of 150 ml/hour (=29 ml/hour/cm$^2$), and effluent fractions of 24 ml were collected. The conditions of chromatography and the elutiogram are shown in FIG. 4.

The column was eluted (washed) first with water. After full washing out, elution was continued with a 5 mmolar aqueous ammonium hydrocarbonate solution. The peak fractions of this eluate contain the pure, homogeneous component of formula ($A_3$). The ammonium hydrocarbonate fractions comprising the compound of formula ($A_3$) as single component were pooled, a small amount of n-butanol was added, and the mixture was evaporated to almost dryness. Water was evaporated repeatedly from the residue in order to remove the volatile ammonium hydrocarbonate, then the concentrate was dehydrated first with distilled methanol and then with absolute methanol. Finally the substance was precipitated from the concentrate with absolute ether. The separated substance was filtered off on a G4 sintered glass filter, washed with acetone and dried. 190 mg (42%) of a compound of formula ($A_3$) were obtained; m.p.: 159°-161° C., solubility in water: about 5 mg/ml (this decrease in water solubility can be attributed to the presence of some bound $NH_4^+$ and of ammonium hydrocarbonate residues), biological activity (on *Bacillus subtilis*): 0.5-1 /ug/ml.

As mentioned above, the substance was subjected to repeated ion exchange chromatography on carboxymethyl cellulose in $H^+$ cycle in order to remove the contaminations which decrease its water solubility. The substance was applied onto the column as a 2-4 mg/ml aqueous solution, the column was fully washed out with water, and then dehydrated gradually first with distilled methanol and then with absolute methanol. The substance was eluted with absolute methanol comprising 10 mmoles of acetic acid. The effluent was filtered through a G4 sintered glass filter or through a Whatman glass fibre plate, the filtrate was concentrated to a small volume, and the product was precipitated from the concentrate with absolute acetone. Thereafter the method described in the previous paragraph was followed. A pure compound of formula ($A_3$) was obtained; m.p.: 164°-166° C. (in contrast to the initial value of 159°-161° C.), solubility in water: 40-50 mg/ml. The repeated ion exchange chromatography resulted in a material loss of maximum 10%.

EXAMPLE 4

Preparation of the Component of Formula ($A_1$)

In the method described in Example 3 the component of formula ($A_3$) was eluted, whereas the component of formula ($A_1$) remained bound to the carboxymethyl cellulose column in $NH_4^+$ cycle. The component of formula ($A_1$) was removed from the column as follows:

The column was washed with water to remove ammonium hydrocarbonate completely, and then it was gradually dehydrated first with distilled methanol and then with absolute methanol. Thereafter the component of formula ($A_1$) was eluted with absolute methanol comprising 10 mmoles of acetic acid. The effluents were pooled, filtered through a G4 sintered glass filter, evaporated to a small volume, and the product was precipitated from the concentrate with absolute acetone. Thereafter the method described in Example 3 was followed.

150 mg (33%, calculated for the amount of the starting substance applied in Example 3) of the component of formula (A$_1$) were obtained; m.p.: 164°–168° C., solubility in water: 50 mg/ml, biological activity (on *Bacillus subtilis*): 0.03–0.06 /ug/ml.

What we claim is:

1. A process for preparing water soluble primycin, which comprises reacting water insoluble primycin having a water solubility of 0.04 mg/ml in a C$_{1-3}$ alcohol with a condensable substance comprising a C—C—C bridge selected from the group consisting of ethyl cyanoacetate, malonic acid dinitrile and acetyl acetone, in the presence of sodium or potassium methoxide or ethoxide, the resulting primycin product having a water solubility of 40–60 mg/ml.

2. The process of claim 1, wherein the C$_{1-3}$ alcohol is ethanol.

3. The process of claim 1, wherein said reaction is carried out in the presence of sodium methoxide.

4. The process of claim 1, wherein said reaction is carried out in the presence of 15–20 ppm of lead introduced as a soluble lead compound.

5. The process of claim 4, wherein lead acetate is applied as a soluble lead compound.

6. The process of claim 1, wherein the condensable substance comprising a C—C—C bridge is ethyl cyanoacetate.

7. The process of claim 1, wherein the condensable substance comprising a C—C—C bridge is malonic acid dinitrile.

8. The process of claim 1, wherein the condensable substance comprising a C—C—C bridge is acetyl acetone.

9. The process of claim 1, which further comprises applying the resulting primycin product to a silica gel column, and eluting with an approximately 1% aqueous solution of Partridge mixture as eluting agent to obtain a mixture of components (A$_1$) and (A$_3$), both of the formula

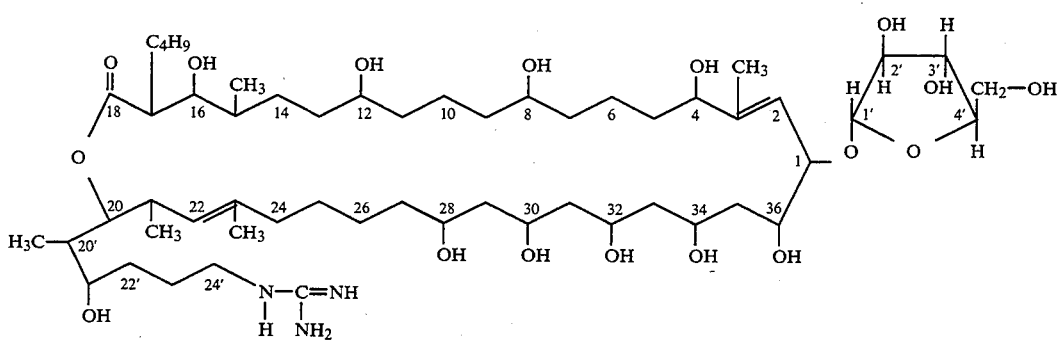

said mixture having a water solubility of about 50 mg/ml.

10. The process of claim 9, which further comprises subjecting the mixture of components of formula (A$_1$) and (A$_3$) to ion-exchange chromatography, applying carboxymethyl cellulose in ammonium cycle as absorbent, and eluting said absorbent with aqueous ammonium hydrocarbonate solution to obtain the pure component of formula (A$_3$) with a water solubility of about 50 mg/ml.

11. The process of claim 10, which further comprises continuing the elution of the carboxymethylcellulose absorbent with absolute methanol containing about 10 moles of acetic acid until the component of formula (A$_1$) with a water solubility of about 10 mg/ml in pure form is obtained.

12. An antibacterial pharmaceutical or veterinary composition, wherein water soluble primycin prepared according to the process of claim 1 is present in an antibacterial-effective amount as active ingredient, together with a pharmaceutically acceptable carrier, diluent or an auxiliary agent.

13. An antibacterial pharmaceutical or veterinary composition, wherein a water-soluble mixture of the components of formula (A$_1$) and (A$_3$), prepared according to the process of claim 9, is present in an antibacterial-effective amount as active ingredient, together with a pharmaceutically acceptable carrier, diluent or an auxiliary agent.

14. An antibacterial pharmaceutical or veterinary composition, wherein a water-soluble single compound of formula (A$_3$), prepared according to the process of claim 10, is present in an antibacterial-effective amount as active ingredient, together with a pharmaceutically acceptable carrier, diluent or an auxiliary agent.

15. An antibacterial pharmaceutical or veterinary composition, wherein a water-soluble single compound of the formula (A$_1$) prepared according to the process of claim 11 is present in an antibacterial-effective amount as active ingredient, together with a pharmaceutically acceptable carrier, diluent or an auxiliary agent.

* * * * *

UNITED STATES PATENT AND TRADEMARK OFFICE
CERTIFICATE OF CORRECTION

PATENT NO.: 5,441,940

DATED: August 15, 1995

INVENTOR(S): KERESZTES et al.

It is certified that error appears in the above-identified patent and that said Letters Patent is hereby corrected as shown below:

Column 16, claim 10, lines 4 and 5, replace "absorbent", both occurrences, with --adsorbent--.

Signed and Sealed this

Seventeenth Day of October, 1995

Attest:

BRUCE LEHMAN

Attesting Officer

Commissioner of Patents and Trademarks